United States Patent [19]

Makisumi et al.

[11] Patent Number: 5,091,539
[45] Date of Patent: Feb. 25, 1992

[54] AZOLYL CYCLOALKANOL DERIVATIVES AND AGRICULTURAL FUNGICIDES

[75] Inventors: Yasuo Makisumi, Hyogo; Akira Murabayashi, Osaka; Takayuki Hatta; Takeo Ishiguro, both of Shiga, all of Japan

[73] Assignee: Shionogi & Co., Ltd., Osaka, Japan

[21] Appl. No.: 531,347

[22] Filed: May 31, 1990

Related U.S. Application Data

[60] Division of Ser. No. 229,790, Aug. 4, 1988, abandoned, which is a continuation of Ser. No. 22,067, Mar. 5, 1987, abandoned, which is a continuation of Ser. No. 696,432, Jan. 30, 1985, abandoned.

[30] Foreign Application Priority Data

Feb. 3, 1984 [JP] Japan .................... 59-18564
Feb. 15, 1984 [JP] Japan .................... 59-27905

[51] Int. Cl.$^5$ .................... C07D 249/08; C07D 233/60
[52] U.S. Cl. ............................ 548/267.8; 548/262.2; 548/266.2; 548/266.6; 548/341
[58] Field of Search .................... 548/262.2, 341, 336, 548/267.8

[56] References Cited

U.S. PATENT DOCUMENTS

| | | | |
|---|---|---|---|
| 3,636,002 | 1/1972 | Godefrai et al. | 260/309 |
| 4,079,062 | 3/1978 | Van Reet et al. | 548/262 |
| 4,289,526 | 9/1981 | Worthington et al. | 71/92 |
| 4,380,546 | 4/1983 | Sanfer et al. | 548/268.6 |
| 4,414,210 | 11/1983 | Miller et al. | 568/645 |
| 4,431,815 | 2/1984 | Thorogood | 548/335 |
| 4,503,062 | 3/1985 | Gravestock | 548/262 |
| 4,554,007 | 11/1985 | Funaki et al. | 514/383 |

FOREIGN PATENT DOCUMENTS

| | | |
|---|---|---|
| 722813 | 4/1969 | Belgium . |
| 0011770 | 6/1980 | European Pat. Off. . |
| 015639 | 9/1980 | European Pat. Off. . |
| 0019359 | 11/1980 | European Pat. Off. . |
| 2244761 | 3/1974 | Fed. Rep. of Germany . |
| 2654890 | 6/1977 | Fed. Rep. of Germany . |
| 2370432 | 6/1978 | France . |
| 1445707 | 8/1976 | United Kingdom . |
| 1464224 | 2/1977 | United Kingdom . |

OTHER PUBLICATIONS

Il Farmaco, Edizione Scientifica, Anno XXVI, No. 11, Nov., 1971, pp. 931-940.

*Primary Examiner*—Patricia L. Morris
*Attorney, Agent, or Firm*—Wenderoth, Lind & Ponack

[57] ABSTRACT

Novel 1-substituted -2-imidazolyl (or 1,2,3-triazolyl)cyclohexanols or cycloheptanols having anti-fungal activity against wide range of agricultural fungi with vapor effect.

1 Claim, No Drawings

AZOLYL CYCLOALKANOL DERIVATIVES AND AGRICULTURAL FUNGICIDES

This application is a division of application Ser. No. 229,790, filed Aug. 4, 1988, now abandoned, which application is a continuation of now abandoned application Ser. No. 022,067, filed Mar. 5, 1987, which application is, in turn, a continuation of now abandoned application Ser. No. 696,432, filed Jan. 30, 1985.

BACKGROUND OF THE INVENTION

Some triazolylalkanols are known to be effective as agricultural fungicides (British Patent Publication A-1464224). The European Patent Publication No. A1-0094146 discloses that 1-phenyl (or substituted phenyl)-2-imidazolyl (or triazolyl)cycloalkanol derivatives are generally active against fungi. In the derivatives, the neighboring azolyl and hydroxy may be positioned in cis or trans configuration. The latter specification, however, discloses only a process which is supposed to give trans-isomers as the main product when deduced from reaction mechanism. The compounds shown in the working examples are recognized as trans-isomers from the physical constants. Furthermore, the specification refers to none of the differences in anti-fungal activity caused by the difference of the configuration between cis and trans forms. Especially, it does not suggest the specificity of the cis-isomer of the present invention.

SUMMARY OF THE INVENTION

This invention relates to azolylcycloalkanol derivatives, the salts and the process for preparing the same. Further, it relates to an agricultural fungicide containing the above compound as active ingredient.

This invention includes novel imidazolyl- or triazolyl-cycloalkanols having an alkyl, aralkyl or heterocyclic ring group at the 1 position, of which strong antimicrobial, especially anti-fungal activity is not known. Further, cis-1-phenyl (or substituted phenyl)-2-imidazolyl (or triazolyl)-cycloalkanols are not known to have anti-fungal activity against wide range of agricultural fungi with vapor effect.

The objective compounds of this invention are represented by the formula I:

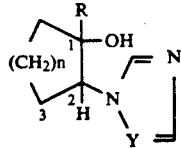

wherein R is alkyl, phehyl, benzyl, thienyl or naphthyl, being optionally substituted by one or more halogens, Y is methine or nitrilo and n is 2 or 3 with the proviso that azolyl and hydroxy are in cis configuration when R is phenyl or halogenophenyl.

DETAILED EXPLANATION OF THE INVENTION

This invention includes 1-substituted-2-imidazolyl- (or 1,2,4,-triazol-1-yl)cyclohexanols and cycloheptanols.

The compounds I may take the cis and trans configuration as noted above. In this specification, the trans and cis isomers are decided in the relation of the hydroxy at the position 1 and the azolyl at the position 2. This invention includes cis-isomers and trans-isomers as well as both enantiomers except for the trans-isomers of the compounds I of which R is phenyl or halogenophenyl. Additionally, this invention includes the salts of the compounds I, for example, salts with an inorganic acid (e.g. hydrochloride, hydrobromide, hydroiodide, and phoshate) and salts with an organic acid (e.g. acetate, citrate, maleate, malate, succinate, tartarate, cinnamate and benzoate).

In the above definition, alkyl means $C_1$ to $C_5$ straight or branched alkyl such as methyl, ethyl, propyl, isopropyl, butyl, isobutyl, t-butyl, pentyl, isopentyl and the like. Halogen includes fluorine, chlorine, bromine and iodine.

Thus, the group R in the compounds I may be alkyl, halogenoalkyl, phenyl, haogenophenyl, thienyl, halogenothienyl, naphthyl or halogenonaphthyl with the proviso that the group R and hydroxy form the cis configuration when R is phenyl or halogenophenyl. The halogen may be located at any position of the group R and the number of halogens is not limited. Preferable R is, for example, 2-chlorophenyl, 2-fluorophenyl, 3-chlorophenyl, 4-chlorophenyl, 4-fluorophenyl, 2,4-dichlorophenyl, 2,5-dichlorophenyl, 3,4-dichlorophenyl, benzyl, 2-chlorobenzyl, 4-chlorobenzyl, 2,4-dichlorobenzyl, 4-fluorobenzyl, 2,4-difluorobenzyl, 2-thienyl, 5-chloro-2-thienyl, 5-iodo-2-thienyl, 3,5-dichloro-2-thienyl, 3,4,5-trichloro-2-thienyl, 1-naphthyl and the like. The more preferable R groups are, for example, 2-chlorophenyl, 4-chlorophenyl, 4-fluorophenyl, 2,5-dichlorophenyl, 5-chloro-2-thienyl, 3,4,5-trichloro-2-thienyl, naphthyl and the like. Y is methine or nitrilo and nitrilo is preferable.

The compounds I are prepared by several processes and the main product may be in cis-form or trans-form depending on the process. The process for preparing each isomer is shown below. In the following scheme, cis-or transisomer alone is illustrated without referring to the enantiomer to be produced at the same time, which should not be construed that the other enantiomer is not produced.

PROCESS (1)

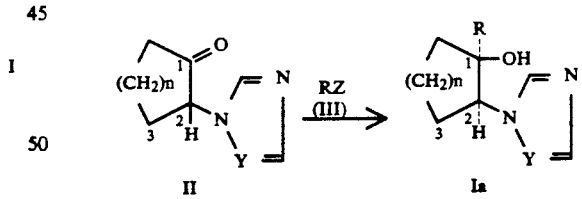

(wherein Z is halomagnesium or an alkali metal and R, Y and n each has the same significance as noted above.)

The process consists of introduction of the substituent R into the position 1 of a cycloalkanone of the formula II to give a cycloalkanol (Ia); namely, reaction of a Compound II with a Grignard reagent or an alkali metal compound of the above formula III having a desired substituent to give cisisomer (Ia) as main product.

It is practised in an ether solvent (e.g. tetrahydrofuran, diglyme, ether or isopropyl ether) or in a mixed medium such as benzene slovent (e.g. benzene or toluene) containing an ether solvent. The ether solvent alone is preferably used as reaction medium. The reaction is generally practised under cooling.

Among the starting compounds II, (1,2,4-triazol-1-yl)cyclohexanone is a known compound disclosed in the British Patent Publication No. 1464224-A. Other Compounds II can be easily prepared as shown by the following reaction scheme.

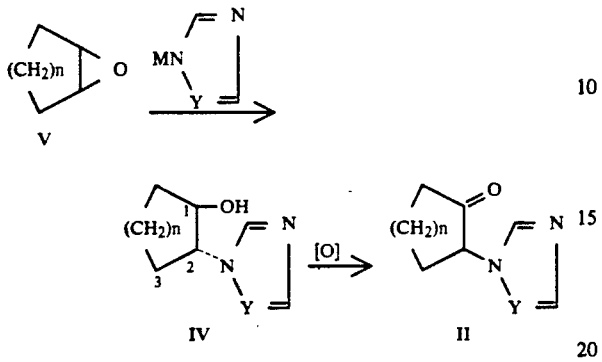

(wherein M is hydrogen or an alkali metal and Y and n each has the same significance as noted above).

The reaction of cycloalkene oxide (V) with imidazole, 1,2,4-triazol or its alkali salt (e.g. sodium or potassium salt) of the formula VI is effected in a solvent or without solvent at room temperature or under heating to give 2-azolylcycloalkanol (IV). As the reaction solvent, polar organic solvents are preferable. They are, for example, alcohols (e.g. methanol, ethanol, propanol and isopropanol), dimethylformamide, dimethylacetamide and the like. Dimethylformamide and dimethylacetamide are favorable when Compound VI is an alkali metal salt. The reaction may be effected in the presence of a Lewis acid when Compound VI is a free base.

The resulting Compound IV is oxidized to give the desired 2-azolylcycloalkanone (II). The oxidation is effected, for example, by the reaction with an acid anhydride (e.g. trifluoroacetic anhydride or acetic anhydride) or oxalyl chloride and dimethylsulfoxide in methylene chloride followed by treatment with an organic base (e.g. triethylamine or pyridine).

The thus prepared compound is separated and purified by the usual methods such as extraction, recrystallization, chromatography and the like and made in to a desired salt, if necessary.

PROCESS (2)

The process for preparing a trans-isomer as main product is mostly effected in the nearly the same manner as that disclosed in the European Patent Publication No. A₁-0094146 as shown below.

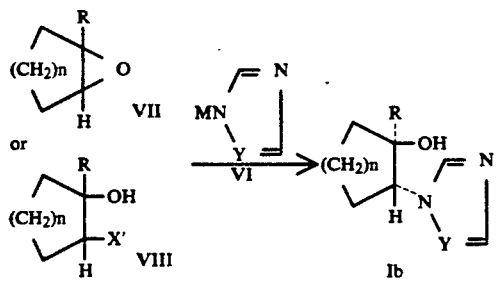

(wherein X' is bromine or chlorine and R, Y, n and M each represents the same significance as noted above).

(i) As shown in the above scheme, 1-substituted cycloalkene oxide (VII) is made to react with imidazole, 1,2,4-triazole or its salt (e.g. sodium or potassium salt) without solvent or in a medium such as an alcohol solvent (e.g. methanol, ethanol, propanol or isopropanol), dimethylformamide, dimethylacetamide or the like at room temperature or under heating. The reaction can be effected under the same condition as in that of the above-noted Compound V with Compound VI.

(ii) Cycloalkane halohydrin (VIII) is made to react with Compound VI in an inactive organic solvent (e.g. dimethylformamide or dimethylacetamide) at room temperature or under heating, preferablly at about 20° to about 100° C. The reaction may be effected in the presence of an acid condensing agent if Compound VI is a free base, i.e. imidazole or triazole. As the acid condensing agent, an excess amount of Compound VI can be used or an organic base (e.g. pyridine or triethylamine) can be added to the reaction mixture.

The starting compound VII and VIII can be prepared from cyclohexanone or cycloheptanone as shown below.

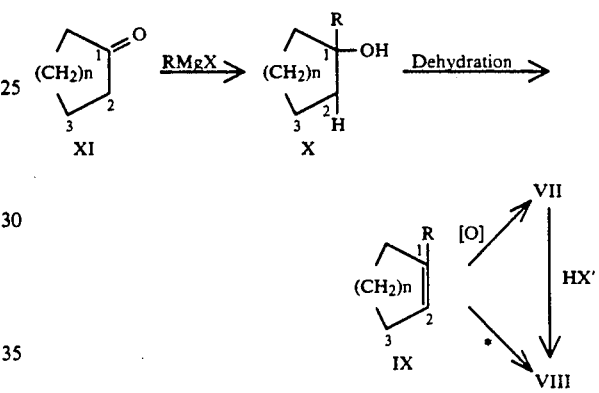

* = formation of halohydrin (wherein R, n and X' each has the same significance as noted above).

Cycloalkanone (XI) is subjected to the similar Grignard reaction as noted in the above (1) and the resulting tertiary alcohol (X) is applied to dehydration, e.g. by heating with a catalysis (e.g. p-toluenesulfonic acid) to give 1-substituted cycloalkene (IX). Successively, Compound IX is oxidized with a peracid (e.g. m-chloroperbenzoic acid, perbenzoic acid, performic acid or peracetic acid) to give cycloalkene oxide (VII). Alternatively, Compound IX is converted into halohydrin to give cycloalkane halohydrin (VIII). Compound IX, for example, is made to react with N-bromoacetamide (NBA), N-bromosuccinimide (NBS) or N-chlorosuccinimide (NCS) in an aqueous solvent (e.g. aqueous acetone, aqueous dimethylsulfoxide, aqueous tetrahydrofuran or aqueous dioxane) under cooling or at room temperature or reacted with bromine/potassium bromide in water to give Compound VIII. Compound VIII can be prepared by reaction of Compound VII with hydrogen halide.

The desired Compound I can be prepared by the above processes alone while halogenated Compound I can also be prepared by halogenation of nonhalogenated Compound I obtained by the above processes.

The thus prepared compound is separated and purified by the usual methods such as extraction, recrystallization, chromatography and the like and made into a desired salt, if necessary.

The compound I and the salts have strong antimicrobial activity, especially against fungi infecting agricultural products and are useful as fungicides for agricultural products, seeds, seedlings and the like. The anti-fungal activity against typical agricultural fungi is shown below. In the following tests, the test compounds are represented by the numbers used in the working examples.

TEST 1

Control Test to Damping-Off of Cucumber (1) The fungus causing damping-off of cucumber seedlings, Rhizoctonia solani or Fusarium oxysporum was cultured on a wheat bran medium at 28° C. for 5 days, which was mixed with sterilized soil and cultured for 2 days to prepare the inoculum. Sterilized soil (150 g) was put into a pot of 9 cm in diameter. The surface of the spot was covered with the above inoculum. A solution (30 ml) at a concentration of 500 ppm or 31.3 ppm the test compound was poured into each pot, which was then dried. Twenty cucumber seeds (Cultivar: Matsukaze) were sown 2 days after. The pots were kept at 30°±2° C. for 14 days. The infection was observed 14 days after and disease degree and percent disease degree were obtained by setting an evaluation index for each disease sympton.

(2) Evaluation i. Percent disease degree (%) for Rhizoctonia solani =

$$\frac{4a + 3b + 2c + d}{4(a + b + c + d + e)} \times 100$$

wherein
a: number of seeds without germination
b: number of seedlings showing damping-off
c: number of wilted seedlings
d: number of seedlings being a little brownish in cotyledons or at the bottom of the stem
e: number of uninfected seedlings ii. Percent disease degree (%) for Fusarium oxysporum =

$$\frac{3a + 2b + c}{3(a + b + c + d)} \times 100$$

wherein
a: number of seeds without germination or seedlings with damping-off
b: number of wilted seedlings
c: number of seedlings being a little brownish in cotyledons or at the bottom of the stem
d: number of uninfected seedlings iii. Percent disease control (%)

$$\frac{\text{Disease degree in untreated plot} - \text{Disease degree in treated plot}}{\text{Disease degree in untreated plot}} \times 100$$

(3) Results

TABLE 1

| Test Comp. | Concentration (ppm) | Rhizoctonia solani | | Fusarium oxysporum | |
|---|---|---|---|---|---|
| | | Disease Degree | Percent Disease Control (%) | Disease Degree | Percent Disease Control (%) |
| 12 | 500 | 0 | 100 | 17 | 83 |
| 13 | 500 | 5 | 95 | 100 | 0 |
| 28 | 31.3 | 8 | 92 | — | — |
| 30 | 31.3 | 18 | 82 | — | — |
| 32 | 31.3 | 10 | 90 | — | — |
| Captan | 800 | — | — | 0 | 100 |
| Mepronil | 750 | 5 | 95 | — | — |
| " | 47 | 77 | 23 | — | — |
| Untreated | — | 100 | 0 | 100 | 0 |

TEST 2

Control Test of Botrytis Rot (Gray Mold) of Cucumber (1) Seedlings of cucumber (Cultivar: Matsukaze) were planted in a pot of 9 cm in diameter. The first leaf was sprayed with 3 ml each of solutions containing the test compound at the concentration of 125 or 31.3 ppm and the plant was dried by the air. After inoculation of the spores of Botrytis cinerea, the plants were kept at 20°±2° C. and 90-100% humidity ((i) protective spraying). Alternatively, the spores were inoculated at first and when the leaves suffered a little (about 2 days after), the solutions of the test compounds were sprayed ((ii) curative spraying). Evaluation was practised 3 days after the inoculation. Percent disease control was calculated by the ratio of diameter of diseased area in treated and untreated plants.

(2) Evaluation

Percent disease control (%) =

$$\frac{\text{Diameter of diseased area in untreated plot} - \text{Diameter of diseased area in treated plot}}{\text{Diameter of diseased area in untreated plot}} \times 100$$

(3) Results

TABLE 2

| Test Compound | Concentration (ppm) | Percent Disease Control | |
|---|---|---|---|
| | | Protective Spraying | Curative Spraying |
| 13 | 125 | 100 | 94 |
| 22 | 125 | 100 | 89 |
| | 31.3 | 100 | 46 |
| 24 | 125 | 100 | 94 |
| | 31.3 | 100 | 86 |
| 28 | 125 | 100 | 79 |
| | 31.3 | 40 | 48 |
| 30 | 125 | 100 | 94 |
| | 31.3 | 89 | 86 |
| Iprodione | 125 | 100 | 90 |
| | 31.3 | 100 | 64 |
| Untreated | — | 0 | 0 |

TEST 3

Control Test to Sclerotinia Rot of Cucumber (1) This test was practised in the same manner as in the above test, control test of Botrytis rot (gray mold) of cucumber, except for using the mycelium of Sclerotinia sclerotiorum as inoculm.

(2) Evaluation
The same as in test 2.

(3) Results

TABLE 3

| Test Compound | Concentration (ppm) | Percent Disease Control (%) Protective Spraying | Curative Spraying |
|---|---|---|---|
| 13 | 125 | 100 | 95 |
| 22 | 125 | 100 | 95 |
|    | 31.3 | 67 | 93 |
| 24 | 125 | 100 | 97 |
|    | 31.3 | 100 | 96 |
| 28 | 125 | 80 | 97 |
|    | 31.3 | 56 | 77 |
| 30 | 125 | 100 | 96 |
|    | 31.3 | 89 | 94 |
| 32 | 125 | 100 | 94 |
|    | 31.3 | 72 | 86 |
| Iprodione | 125 | 100 | 90 |
|    | 31.3 | 100 | 77 |
| Untreated | — | 0 | 0 |

TEST 4

Control Test to Powdery Mildew of Cucumber (1) Seeds of cucumber (Cultivar: Matsukaze) were sown in a pot of 9 cm in diameter and the pots were kept in a green house until the plant was grown for 2-3 leaf stage. The first leaf was sprayed with, (i) 3 ml each of solutions containing the test compound at the prescribed concetrations and dried by the air (foliar treatment). Inoculation of spore suspension of *Sphaerotheca fuliginea* by spraying was practised 2 days before the treatment (curative effect) or 1 day after the treatment (protective effect). Alternatively, (ii) 5 ml of the solution was applied at the root of the seedlings (soil treatment). The pots were kept in a greenhouse for 2 days and inoculation was practised in the same manner noted above. (iii) After sprayed with 3 ml of a solution of the test compound at a concentration of 125 ppm and dried by the air, the treated pots were set in a greenhouse. Untreated pots were placed next to the treated pots. Those treated and untreated plants were inoculated with spore suspension. Protective effect of the test compounds by vapor was thus checked. The effect was examined 14 days after the inoculation of the spores.

(2) Evaluation

The results of both foliar and soil treatments were represented by the following index.

0: Disease sign is observed on the whole leaf.
3: Disease sign is observed on the leaf in about 50%.
5: Disease sign is observed on the leaf in about 30%.
7: Disease sign is observed on the leaf in about 20%.
9: a little disease sign is observed.
10: No sign is observed.

Vapor effect is shown by positive (+) or negative (−), 9-10 and 0-3 in the above index respectively.

(3) Results

TABLE 4

| Test Compound | Concentration (ppm) | Protective Index Foliar Treatment | Soil Treatment | Vapor Effect |
|---|---|---|---|---|
| 1 | 125 | 10 | 5 | + |
| 3 | 125 | 10 | 10 | + |
| 5 | 125 | 10 | 3 | + |
| 6 | 125 | 10 | 0 | − |
| 12 | 125 | 10 | 10 | + |
| 13 | 125 | 10 | 10 | + |
| Chinomethionat | 125 | 10 | — | — |
| Dimethirimol | 500 | — | 5 | — |
| Untreated | — | 0 | 0 | — |

TABLE 4

| Test Compound | Cencentration (ppm) | Foliar Treatment Protective Effect | Curative Effect | Soil Treatment Protective Effect |
|---|---|---|---|---|
| 22 | 31.3 | 10 | 10 | 10 |
|    | 7.8 | 10 | 10 | 10 |
|    | 2.0 | 10 | 10 | 5 |
|    | 0.5 | 5 | 10 | 0 |
| 23 | 31.3 | 10 | 10 |  |
|    | 7.8 | 10 | 10 |  |
|    | 2.0 | 5 | 3 |  |
|    | 0.5 | 0 | 0 |  |
| 24 | 31.3 | 10 | 10 | 10 |
|    | 7.8 | 10 | 10 | 10 |
|    | 2.0 | 10 | 10 | 0 |
|    | 0.5 | 5 | 10 | 0 |
| 26 | 31.3 | 10 | 10 |  |
|    | 7.8 | 9 | 9 |  |
|    | 2.0 | 3 | 7 |  |
|    | 0.5 | 0 | 0 |  |
| 27 | 31.3 | 10 | 10 |  |
|    | 7.8 | 9 | 10 |  |
|    | 2.0 | 3 | 5 |  |
|    | 0.5 | 0 | 0 |  |
| 28 | 31.3 | 10 | 10 | 10 |
|    | 7.8 | 10 | 10 | 10 |
|    | 2.0 | 5 | 9 | 5 |
|    | 0.5 | 0 | 5 | 0 |
| 29 | 31.3 | 10 | 10 |  |
|    | 7.8 | 9 | 9 |  |
|    | 2.0 | 3 | 3 |  |
|    | 0.5 | 0 | 0 |  |
| 30 | 31.3 | 10 | 10 | 10 |
|    | 7.8 | 10 | 10 | 10 |
|    | 2.0 | 9 | 10 | 0 |
|    | 0.5 | 0 | 7 | 0 |
| 31 | 31.3 | 10 | 10 |  |
|    | 7.8 | 9 | 10 |  |
|    | 2.0 | 0 | 9 |  |
|    | 0.5 | 0 | 3 |  |
| 32 | 31.3 | 10 | 10 | 10 |
|    | 7.8 | 10 | 10 | 10 |
|    | 2.0 | 9 | 10 | 0 |
|    | 0.5 | 0 | 7 | 0 |
| 33 | 31.3 | 10 | 10 | 0 |
|    | 7.8 | 10 | 10 | 0 |
|    | 2.0 | 5 | 10 | 0 |
|    | 0.5 | 0 | 3 | 0 |
| 34 | 31.3 | 10 | 10 | 0 |
|    | 7.8 | 9 | 10 | 0 |
|    | 2.0 | 0 | 10 | 0 |
|    | 0.5 | 0 | 5 | 0 |
| 35 | 31.3 | 10 | 10 | 10 |
|    | 7.8 | 10 | 10 | 9 |
|    | 2.0 | 10 | 10 | 0 |
|    | 0.5 | 5 | 10 | 0 |
| Triadimefon | 31.3 | 10 | 10 | 10 |
|    | 7.8 | 9 | 10 | 3 |
|    | 2.0 | 7 | 9 | 0 |
|    | 0.5 | 0 | 0 | 0 |
| Untreated | — | 0 | 0 | 0 |

TEST 5

Control Test of Crown Rust of Oat (1) Young oats (Cultivar: Pc38) grown in pots in a greenhouse were (i) sprayed with 10 ml each of solution of the test compounds at a prescribed concentration and after air-drying, they were inoculated with 15 mg of uredospores of *Puccinia coronata* per 20 pots (protective spraying) or (ii) sprayed with the test solution 3 days after inoculation of uredospores. After each plant was kept at 20°–25° C. in a greenhouse for 2 weeks, number of uredia was counted on the first leaf.

(2) Evaluation

Percent disease control (%) =

$$\frac{\text{Number of uredia in untreated plot} - \text{Number of uredia in treated plot}}{\text{Number of uredia in untreated plot}} \times 100$$

(3) Result

TABLE 5

| Test Compound | Concentration (ppm) | Percent Disease Control | |
|---|---|---|---|
| | | Protective Spraying | Curative Spraying |
| 1 | 125 | 100 | 100 |
| 22 | 50 | 100 | 100 |
| | 25 | 100 | 88 |
| | 12.5 | 100 | 64 |
| Triadimefon | 125 | 100 | 100 |
| Fenarimol | 50 | 100 | 98 |
| | 25 | 89 | 92 |
| | 12.5 | 62 | 75 |
| Untreated | — | 0 | 0 |

TEST 6

Control Test to Powdery Mildew of Cucumber by Vapor (1) The first leaves of young cucumber (Cultivar: Matsukaze) planted in pot of 9 cm in diameter were inoculated with spore suspension of *Sphaerotheca fuliginea*. After the plants were kept in a greenhouse for 2 days, thin cover plates, 15 mm in diameter, were put on the first leaves. Filter paper disks soaked with 80 μl of test solution at a concentration of 31.3, 7.8, 2.0 or 0.5 ppm were put on the plates for 3 days. Disease degrees were observed 14 days after the inoculation.

(2) Evaluation

It is evaluated as + when an inhibition zone was observed around the plate, as ± when the inhibition zone has nearly the same diameter (8 mm) as that of plate or as − when there is no inhibition zone.

(3) Results

TABLE 6

| Test Compound | Concentration (ppm) | Protective Effect by Vapor |
|---|---|---|
| 22 | 31.3 | + |
| | 7.8 | + |
| | 2.0 | − |
| | 0.5 | − |
| 30 | 31.3 | + |
| | 7.8 | + |
| | 2.0 | − |
| | 0.5 | − |

TABLE 6-continued

| Test Compound | Concentration (ppm) | Protective Effect by Vapor |
|---|---|---|
| Triadimefon | 31.3 | — |
| | 7.8 | — |
| | 2.0 | — |
| | 0.5 | — |
| | 0.5 | — |
| Untreated | — | — |

TEST 7

Anti-Fungal Activity in vitro (1) Each test compound was diluted by two-fold dilution with GY medium (2% glucose and 0.4% yeast extract) containing 0.01% Tween 80 (trademark). Every diluted solution was inoculated with spore suspension ($10^{5-5}$ spores/ml) of *Alternaria kikuchiana* or a hyphae disk with agar (4 mm in diameter) of other fungi and incubated at 28° C. for 2 days.

(2) Evaluation

The growth of hyphae was observed with the naked eye and the minumum inhibition concentrations were obtained.

TABLE 7

| Test Fungus | Test Compound MIC (μg/ml) | | | | |
|---|---|---|---|---|---|
| | 12 | 22 | 24 | 32 | Fenarimol |
| Monilinia fructicola | 1.56 | 0.78 | 0.2 | 0.39 | 3.13 |
| Cochiobolus sativus | 3.13 | 6.25 | 6.25 | 3.13 | 1.56 |
| Pyrenophora graminea | 6.25 | 12.5 | 12.5 | 1.56 | 12.5 |
| Diaporthe citri | 3.13 | 12.5 | 25.0 | 3.13 | >50.0 |
| Ustilago nuda | 6.25 | 12.5 | 1.56 | 3.13 | 25.0 |
| Corticium rolfsii | 1.56 | >50.0 | 50.0 | 12.5 | 25.0 |
| Alternaria kikuchiana | 25.0 | 50.0 | 12.5 | 3.13 | 6.25 |
| Vasla ceratosperma | 3.13 | ND | ND | ND | 12.5 |
| Cladosporium herbarum | ND | 6.25 | 6.25 | 1.56 | >50.0 |

ND: Not Done

TEST 8

Comparative Test of cis- and trans-isomers

Each cis- and trans-isomers of 1-(4-chlorophenyl)-2-(1,2,4-triazol-1-yl)cyclohexanol (Compound 22 and the trans-isomer)) and 1-(4-fluorophenyl)-2-(1,2,4-triazol-1-yl)cyclohexanol (Compound 28 and the trans-isomer) are subjected to control test to powdery mildew of cucumber and to Borytis rot (gray mold) of cucumber. Each cis isomer has about 4–16 times more effective than the corresponding trans isomer as shown in Table 8.

(1) Test methods and evaluation are the same as those in Tests. 2, 4 and 6.

(2) Results

The results are shown in Table 9.

TABLE 9

| Test Item | | Control Test of Powdery Mildew | | | | Control Test of Gray Mold | | |
|---|---|---|---|---|---|---|---|---|
| | | Foliar Treatment | | Soil Treatment | | | Percent Disease Control (%) | |
| Test Compound | Concentration (ppm) | Protective Effect | Curative Effect | Protective Effect | Vapor Effect | Concentration (ppm) | Protective Spraying | Curative Spraying |
| 22 | 31.3 | | | 10 | + | 125 | 78 | 82 |
| | 7.8 | | | 10 | ± | 31.3 | 62 | 88 |
| | 2.0 | 10 | 10 | 10 | − | 7.8 | 35 | 20 |
| | 0.5 | 10 | 10 | 0 | | | | |
| | 0.12 | 9 | 10 | | | | | |

TABLE 9-continued

| Test Item Test Compound | Concentration (ppm) | Control Test of Powdery Mildew | | | | Control Test of Gray Mold | | |
|---|---|---|---|---|---|---|---|---|
| | | Foliar Treatment | | Soil Treatment | | Concentration (ppm) | Percent Disease Control (%) | |
| | | Protective Effect | Curative Effect | Protective Effect | Vapor Effect | | Protective Spraying | Curative Spraying |
| | 0.03 | 0 | 9 | | | | | |
| Trans-isomer of Compound 22 | 31.3 | | | 5 | — | 125 | 3 | 2 |
| | 7.8 | | | 0 | — | 31.3 | 3 | 0 |
| | 2.0 | 10 | 9 | 0 | — | 7.8 | 0 | 0 |
| | 0.5 | 3 | 5 | 0 | | | | |
| | 0.12 | 0 | 0 | | | | | |
| | 0.03 | 0 | 0 | | | | | |
| 28 | 31.3 | | | 10 | + | 125 | 80 | 98 |
| | 7.8 | | | 10 | ± | 31.3 | 70 | 92 |
| | 2.0 | 10 | 10 | 9 | — | 7.8 | 17 | 30 |
| | 0.5 | 5 | 10 | 0 | | | | |
| | 0.12 | 0 | 7 | | | | | |
| | 0.03 | 0 | 0 | | | | | |
| Trans-isomer of Compound 28 | 31.3 | | | 9 | — | 125 | 0 | 9 |
| | 7.8 | | | 0 | — | 31.3 | 5 | 0 |
| | 2.0 | 0 | 9 | 0 | — | 7.8 | 3 | 0 |
| | 0.5 | 0 | 0 | 0 | | | | |
| | 0.12 | 0 | 0 | | | | | |
| | 0.03 | 0 | 0 | | | | | |

As shown above, the compounds (I) of this invention and the salts have extremely strong anti-fungal activity and are useful as agricultural and industrial fungicides.

The compounds I are formulated into an anti-fungal composition for agricultural use comprising as active ingredient about 0.01 to about 90 weight percent of Compound I based on the weight of the composition by mixing with a suitable solid or liquid carrier and other suitable adjuvants such as surfactants, diluents, spreaders, synergists, sticker, dispersant and the like. Solid carriers include talc, clay, bentonite, pyrophyllite, kaolin, diatomaceous earth, silica and the like. Liquid carriers include water, methanol, ethanol, acetone, dimethyl formamide, ether, benzene, xylene, toluene, naphtha and the like. Surfactants include non-ionic surfactants (e.g. polyoxyethylene alkyl phenyl ethers and polyoxyethylene fatty acid esters), anionic surfactants (e.g. alkylbenzene sulfonic acid salts, lignin sulfonic acid salts and dinaphthylmethane sulfonic acid salts) and the like. As stickers, polyvinyl alcohols, CMC, gum arabic and the like may be used.

The anti-fungal composition is formulated into powders, wettable powders, granules, emulsifiable concentrates, suspensions, solutions, fumigants, gases, pastes and the like and is used for sterilizng agricultural products, seedlings, seeds and the like as well as soil. The compounds I, for example, are homogeneously dissolved in a hydrocarbon or an alcohol with a suitable surfactant to give an emulsifiable concentrate or a solution. They are mixed with a mineral powder and with a suitable surfactant, crushed and homogenized to fine powder to give a wettable powder. The thus-prepared composition is diluted with water to a desired concentration and applied. Alternatively, it may be diluted with mineral powder, homoeneously crushed, blended and used as a dust. Finally, the composition is diluted to contain an effective amount of Compound I. Besides, the composition can be combined with other agrochemicals, e.g. insecticides, sterilizers, herbicides, plant-growth regulators, miticides and the like. It also can be mixed with nutrients.

The composition can be used at a lower concentration compared with the fungicides on the market as recognized in the above tests. The concentration is, for example, about 10 to about 1000 ppm, preferably about 5.0 to about 500 ppm, when used for protective or curative spraying.

The compounds I can be applied by soaking the above composition to a suitable material such as paper, rope and cloth and putting them around plants because of the vapor effect.

Additionally, the composition containing a Compound I may be used as an industrial sterilizer for, for example, painting, timber, paper, cloth and the like. One example is that an effective amount of Compound I may be mixed in a paint for a ship to prevent adhearence of shellfish and algae. A sterilizer containing Compound I at an effective concentration may be sprayed on or soaked into wall-paper and wall-cloth.

The following examples are included merely to aid in the understanding of the invention and variations may be made by one skilled in the art without departing from the spirit and scope of the invention. The term THF means tetrahydrofuran in the following examples.

EXAMPLE 1

To a Grignard reagent prepared by adding a solution of α-bromonaphthalene (814 mg) in anhydrous ether (10 ml) to magnesium (110 mg), a solution of 2-(1,2,4-triazol-1-yl)cyclohexanone (Compound IIb) (500 mg) in anhydrous THF (10 ml) was added dropwise with stirring under ice-cooling. The mixture was stirred at room temperature for 1 hour. After evaporation of the THF, water was added to the residual solution, which was then extracted with chloroform. The extract was washed with water, dried and evaporated. The resultant residue was applied to column chromatography on silica gel (15 g). From the chloroform-ether (1:1) fraction, cis-1-(1-naphthyl)-2-(1,2,4-triazol-1-yl)/cyclohexanol, (1) (395 mg) was obtained: mp. 146°–147° C. (ether).

EXAMPLE 2

To a Grignard reagent prepared by adding a solution of p-chlorobenzyl chloride (1.5 ml) in anhydrous ether (10 ml) to magnesium (220 mg), a solution of Compound IIb (1.0 g) in anhydrous THF (10 ml) was added dropwise under ice-cooling. The mixture was stirred at room temperature for 1 hour. Water was added to the mixture, which was then extracted with chloroform. The extract was washed with water and evaporated. The resultant residue was applied to column chromatography on silica gel (30 g). From the ether fraction, cis-1-(4-chlorobenzyl)-2-(1,2,4-triazol-1-yl)cyclohexanol (2) (760 mg) was obtained: mp. 49°–51° C. (ether-hexane).

NMR: δ(CDCl$_3$) (J=Hz) 4.17d-d (J=12, 4), 4.03s

Anal. Calcd. for C$_{15}$H$_{18}$N$_3$OCl: C, 61.75; H, 6.22; N, 14.40; Cl, 12.15 (%). Found: C, 61.38; H, 6.21; N, 14.07; Cl, 12.33 (%).

EXAMPLE 3

To a Grignard reagent prepared by adding a solution of 2,4-dichlorobenzyl chloride (0.8 ml) in anhydrous ether (10 ml) to magnesium (80 mg), a solution of Compound IIb (500 mg) in anhydrous THF (10 ml) was added dropwise under ice-cooling. The mixture was stirred at room temperature for 40 minutes. Water was added to the mixture, which was then extracted with chloroform. The extract was washed with water and evaporated. The resultant residue was applied to column chromatography on silica gel (15 g). From the ether fraction, cis-1-(2,4-dichlorobenzyl)-2-(1,2,4-triazol-1-yl)cyclohexanol (3) (367 mg) was obtained: mp. 129°–130° C. (ether-hexane).

NMR: δ(CDCl$_3$) 4.30d-d (J-12.4), 3.73s

Anal. calcd. for C$_{15}$H$_{17}$N$_3$OCl$_2$: C, 55.23; H, 5.25; N, 12.88; Cl, 21.74 (%). Found: C, 55.11; H, 5.22; N, 12.76; Cl, 21.69 (%).

EXAMPLE 4

To a Grignard reagent prepared by adding a solution of 2,6-dichlorothiophene (24.07 g) in anhydrous THF (100 ml) to magnesium (3.2 g) dropwise, a solution of Compound IIb (20.0 g) in anhydrous THF (150 ml) was added dropwise under ice-cooling for 30 minutes. The mixture was stirred at room temperature for 5 hours. Water was added to the mixture, which was then acidified with 5% hydrochloric acid, successively neutralized with 5% potassium carbonate and extracted with chloroform. The extract was washed with water and evaporated. The resultant residue was applied to column chromatography on silica gel (150 g). From the chloroform and chloroform-methanol (100:1) fractions, cis-1-(5-chloro-2-thienyl)-2-(1,2,4-triazol-1-yl)cyclohexanol (4) (16.65 g) was obtained: mp. 150°–151° C. (ether).

NMR: δ(CDCl$_3$) 4.4d-d (J=12, 4), 5.17s, 1H.

EXAMPLE 5

(1) Cycloheptene (10 g) was dissolved in methylene chloride (400 ml) and 85% m-chloroperbenzoic acid (23 g) was portionally added with stirring under ice-cooling. The mixture was stirred for 10 hours under ice-cooling and at room temperature for 3 hours. The precipitated benzoic acid was filtered off and washed with methylene chloride. The filtrate and the washings were combined and washed with an aqueous solution of sodium thiosulfate, 5% potassium carbonate and water successively. After drying the evaporation of methylene chloride gives cycloheptene oxide (Vb) as oil.

To the product were added propanol (25 ml) and 1,2,4-triazole (8.6 g). The mixture was heated for 4 hours at 100° C. and the propanol was removed by evaporation. After addition of a small amount of water, the residue was extracted with chloroform. The extract was washed with a small amount of water, dried, and evaporated. The resultant residue is recrystallized from ether-hexane to give 2-(1,2,4-triazol-1-yl)cycloheptanol (IVd) (13.3 g) (Yield: 35.8%), Mp. 85°–86° C.

NMR: δ(CDCl$_3$) 1.6–2m 10H, 4(br) 2H, 5.0s 1H, 7.73s 1H, 8.03s 1H.

(2) A solution of dimethylsulfoxide (1.05 g) in methylene chloride (10 ml) was cooled to −78° C. and a solution of trifluoroacetic anhydride (1.65 ml) in methylene chloride (4 ml) was added dropwise thereto. The mixture was stirred for 1 hour under cooling. A solution of Compound IVd (1.63 g) in methylene chloride (18 ml) was added dropwise thereto and the mixture was made to react at −78° C. to room temperature for 1.5 hours and then cooled to −65° C. Triethylamine (3.75 ml) was added thereto and the mixture was stirred at −65°–0° C. for 1 hour. The reaction mixture was made alkaline with 5% potassium hydroxide and extracted with methylene chloride. The extract was washed with water, dried and evaporated. The residue was applied to column chromatography on silica gel (30 g). From chloroform-methanol (100:1) fraction, 1-(1,2,4-triazol-1-yl)cyclohepatanone (IId) (1.16 g) was obtained (yield 72%). Mp. 82°–82.5° C. (ether-hexane).

IR: ν$_{max}$(CHCl$_3$) 1720 cm$^{-1}$.

NMR: δ(CDCl$_3$) 1.5–2.3m 8H, 2.65m 2H, 5.28d-d (J=12, 5) 1H, 7.91s 1H, 8.22s 1H.

(3) To a Grignard reagent prepared from anhydrous ether (10 ml), magnesium (150 mg) and p-chlorobenzyl chloride (966 mg) was added a solution of Compound IId (538 mg) prepared in (2) in THF (10 ml) with stirring under ice-cooling. The mixture was made to react at room temperature for 1 hour and after addition of water, was extracted with chloroform. The extract was washed with water, dried and evaporated. The resultant residue was applied to column chromatography on silica gel (15 g). From the ether fraction, cis-1-(4-chlorobenzyl)-2-(1,2,4-triazol-1-yl)cycloheptanol (5) was obtained as crystal (yield 75%). Mp. 111°–112° C. (ether-hexane).

NMR: δ(CDCl$_3$) 1.63 m 10H, 2.42q (J=14) 2H, 3.63s 1H, 4.23d-d (J=12, −1) 1H, 7.01d (J=9) 2H, 7.22d (J=9) 2H, 7.95s 1H, 8.20s 1H.

Anal. Calcd. for C$_{16}$H$_{20}$NOCl: C, 62.84; H, 6.59; N, 13.74; Cl, 11.59 (%). Found: C, 62.74; H, 6.46; N, 13.54; Cl, 11.61 (%).

EXAMPLE 6

(1) A mixture of cyclohexene oxide (Va) (9.81 g), ethanol (25 ml) and imidazole (13.6 g) was refluxed under heating for 70 hours. The ethanol was evaporated and after addition of a small amount of water, the residue was extracted with chloroform. The extract was washed with a small amount of water, dried and evaporated to give 2-imidazolylcyclohexanol (IVa) (12.7 g) as crystaline residue (Yield 76%). Mp. 133°–134° C.

NMR: δ(CDCl$_3$) 1.3–2.2m 8H, 3.6m 2H, 4.86s 1H, 6.83s 1H, 6.89s 1H, 7.30s 1H.

(2) By the treatment in the same manner as in Example 5(2), 2-imidazolylcyclohexanone (IIa) was obtained (yield 17%). Mp. 104°–105° C.

IR: ν$_{max}$ (CHCl$_3$) 1730 cm$^{-1}$.

NMR: δ(CDCl$_3$) 1.6–2.7m 8H, 4.78d-d (J=12, 4) 1H, 6, 9s 1H, 7.1s 1H, 7.46s 1H.

(3) To a Grignard reagent prepared from anhydrous THF (4 ml), magnesium (41 mg) and 2-bromothiophene (0.18 ml) was added dropwise a solution of Compound IIa (185 mg) in THF (6 ml) at room temperature. The mixture was refluxed under heating for 1 hour. After evaporation of the solvent followed by addition of water, the residue was extracted with chloroform. The extract was washed with water and evaporated. The residue was applied to column chromatography on silica gel (5 g). From the chloroform-methanol (50:1) fraction, cis-1-(2-thienyl)-2-imidazolylcyclohexanol (6) (238 mg) was obtained (yield 85%). Mp. 82°–84° C. (ether).

NMR: δ(CDCl$_3$) 1.7–2.4 (br) 8H, 3.92d-d (J=12, 4) 1H, 4.15 (br) 1H, 6.6–7.1m 6H.

EXAMPLES 7–10

The following compounds were obtained in the same manner as in the above Examples.

TABLE 10

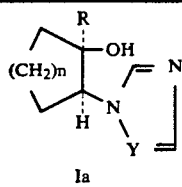

Ia

| Example No. | R | n | Y | Mp (°C.) | NMR: δ (CDCl$_3$) |
|---|---|---|---|---|---|
| 7 | 2-chlorobenzyl | 2 | N | 163–5 | 4.28d-d(J=12, 4)3.73s |
| 8 | 2-thienyl | 2 | N | 131–2 | 4.40d-d(J=11, 4)5.05s |
| 9 | 2-thienyl | 3 | N | 135–6 | 4.45d-d(J=11, −1)5.1s |
| 10 | ethyl | 2 | N | 62–3 | 4.20d-d(J=12, 4)3.67s |

EXAMPLE 11

To a solution of cis-1-(2-thienyl)-2-(1,2,4-triazol-1-yl)cyclohexanol (8) (1.42 g) obtained in Example 8 in methylene chloride (20 ml) was added dropwise 1.81M chlorine-carbon tetrachloride solution (7.9 ml) with stirring under ice-cooling. The mixture was made to react at room temperature for 30 minutes. After addition of an aqueous solution of sodium hydrogencarbonate, the reaction mixture was extracted with methylene chloride. The extract was washed with water, dried and evaporated. The residue was chromatographed on Lober column (Trademark, Merck & Co., Ltd.) and eluted.

From the early fractions, cis-1-(3,4,5-trichloro-2-thienyl)-2-(1,2,4-triazol-1-yl)cyclohexanol (12) (220 mg). Mp. 199°–199.5° C. (acetone-ether).

NMR: δ(CDCl$_3$) 5.23d-d (J=12, 4) 1H, 5.80s 1H.

Successively, cis-1-(3,5-dichloro-2-thienyl)-2-(1,2,4-triazolyl-1-yl)cyclohexanol (11) (380 mg) was obtained. Mp. 174°–175° C. (acetone-ether).

NMR: δ(CDCl$_3$) 5.22d-d (J=12, 4) 1H, 5.67s 1H.

From the latter fractions, cis-1-(5-chloro-2-thienyl)-2-(1,2,4-triazol-1-yl)cyclohexanol (4) (560 mg) was obtained. Mp. 152°–153° C. (ether-hexane).

NMR: δ(CDCl$_3$) 4.4d-d (J=12, 4) 1H, 5.17s 1H.

EXAMPLE 12

A solution of cis-1-(2-thienyl)-2-(1,2,4-triazol-1-yl)cycloheptanol (9) (790 mg) obtained in Example 9 in methylene chloride (25 ml) was added 1.8M chlorine-carbon tetrachloride solution (2.5 ml) under ice-cooling. The mixture was made to react for 10 minutes. After addition of a sodium hydrogencarbonate solution, the mixture was extracted with methylene chloride. The extract was washed with water and evaporated. The residue was applied to column chromatography on silica gel (15 g). From the ether fraction, cis-1-(5-chloro-2-thienyl)-2-(1,2,4-triazol-1-yl)cycloheptanol (13) (585 mg) was obtained. Mp. 170°–173° C.

NMR: δ(CDCl$_3$) 4.38d-d (J=11, −1) 1H, 5.13s 1H.

EXAMPLE 13

(1) To a Grignard reagent prepared from magnesium (26.7 g), 2,5-dichlorothiophene (16.83 g) and anhydrous THF (70 ml) was added dropwise in small portions a solution of cyclohexanone (XIa) (9.815 g) in anhydrous THF (30 ml) with stirring under ice-cooling in nitrogen atmosphere. The mixture was made to react at room temperature for 3 hours and after addition of water and acidification with 5% hydrochloric acid, extracted with chloroform. The extract was washed with water, dried and evaporated. The residue was applied to column chromatography on silica gel (70 g). From the benzene fraction, 1-(5-chloro-2-thienyl)cyclohexanol (Xa) (17.6 g) was obtained as an oil (yield 81.2%).

(2) To a solution of Compound Xa (17.6 g) in toluene (300 ml) was added p-toluenesulfonic acid (500 mg). The resulting water was removed by azeotropic evaporation. The residual solution was cooled, washed with a 5% aqueous solution of potassium carbonate and water successively and evaporated to give 1-(5-chloro-2-thienyl)cyclohexene (IXa) (16.0 g) as an oil.

NMR: δ(CDCl$_3$) 1.67m 4H, 2.25 (Br) 4H, 6.00 (Br) t-like 1H, 6.43d (J-4) 1H, 6.72d (J-4) 1H.

(3) The above Compound IXa (7.0 g) was dissolved in a mixture of acetone (130 ml) and water (20 ml) and thereto added N-bromoacetamide (5.84 g). After stirring at room temperature for 2.5 hours followed by addition of water and a 1% aqueous solution of sodium thiosulfate, the mixture was extracted with chloroform. The extract was washed with water and evaporated to give tran-1-(5-chlorothienyl)-2-bromocyclohexanol (VIIa), as colored oily residue. The residue was dissolved in dimethylacetamide (20 ml) and the solution was added to a solution of sodium triazole prepared from 1,2,4-triazole (4.87 g), dimethylacetamide (30 ml) and 60% sodium hydride (2.11 g). The mixture was made to react at 100° C. for 6 hours and then kept at room temperature for 3 days. After addition of water, the reaction mixture was extracted with ethyl acetate. The extract was washed with water, dried and evaporated. The residue was applied to column chromatography on silica gel (150 g). From the ether fraction crystalline residue (5.53 g) was obtained. The product was recrystallized from ether to give trans-1-(5-chloro-2-thienyl)-2-(1,2,4-triazol-1-yl)cyclohexanol (14) (2.1 g) (mp. 167°–170° C.). Recrystallization from acetone gave Compound 14 (1.75 g) melting at 170°–172° C.

Anal. Cacld. for $C_{12}H_{14}N_3OSCl$: C, 50.79; H, 4.97; N, 14.81; S, 11.30; Cl, 12.49 (%). Found: C, 50.53; H, 4.97; N, 14.67; S, 11.21; Cl, 12.72 (%).

NMR: δ(CDCl$_3$) 1.6–2.5m 8H, 4.43d-d (J=9, 5) 1H, 5.07s 1H, 6.45d (J=4) 1H, 6.63d (J=4) 1H, 7.9s 2H.

EXAMPLE 14

Five parts of Compound 1, 20 parts of propylene alcohol, 5 parts of polyoxyethylene alkyl phenyl ether and 70 parts of water are mixed and dissolved to give a solution, which is diluted so that the effective concentration of Compound 1 is 10–500 ppm and sprayed foliary. (The number of the compound corresponds to that used in the example for preparation. The same will be applied hereinafter.)

EXAMPLE 15

A solution is prepared in the same manner as in Example 14 using Compound 3 instead of Compound 1.

EXAMPLE 16

One part of Compound 5 is mixed with 99 parts of talc to give a dust.

EXAMPLE 17

Twenty-five parts of Compound 6, 8 parts of polyoxyethylene alkyl phenyl ether, 2 parts of sodium alkylbenzenesulfonate and 65 parts of xylene are mixed and dissolved to give a concentrated emulsion, which is diluted so that the effective concentration of Compound 6 is 50–500 ppm and sprayed foliarly.

EXAMPLE 18

Five parts of Compound 12, 90 parts of an equal-weight mixture of bentonite and talc and 5 parts of sodium alkylbenzenesulfonate are mixed, crushed and formulated to granules.

EXAMPLE 19

Fifty parts of Compound 13, 6 parts of sodium alkylbenzene sulfonate, 4 parts of sodium lignine sulfonate and 40 parts of clay are mixed and crushed to give a wettable powder, which is diluted so that the effective concentration of Compound 13 is 10–500 ppm and sprayed to fruit.

EXAMPLE 20

A wettable powder is prepared in the same manner as in Example 19 using Compound 14 instead of Compound 13.

EXAMPLE 21

· (1) A mixture of cyclohexene oxide (Va) (9.81 g), ethanol (25 ml) and imidazole (13.6 g) was refluxed under heating for 70 hours and the ethanol is removed by evaporation. After addition of a small amount of water, the residue was extracted with chloroform. The extract was washed with a saturated aqueous solution of sodium chloride, dried and evaporated to give 2-imidazolylcyclohexanol (IVa) (12.7 g) as crystaline residue (yield 76%). Mp. 133°–134° C. NMR: δ (CDCl3) 1.3–2.2m8H, 3.6m2H, 4.86s1H, 6.83s1H, 6.89s1H, 7.30s1H ppm.

(2) Dimethylsulfoxide (8.46 g) was mixed with methylene chloride (35 ml) and cooled to −76° C. with stirring and after dropwise addition of a diluted solution of trifluoroacetic anhydride (19.71 g) in methylene chloride (10 ml), stirred for 1 hour. A solution of of 2-imidazolylcyclohexanol (IVa) (12.0 g) in methylene chloride (100 ml) was added dropwise thereto for 10 minutes. The mixture was made to react at −76°--20° C. for 1.5 hours, cooled to −55° C. and after dropwise addition of triethylamine (30 ml) at −55° C., stirred for 1 hour at −55° C. After addition of a 5% sodium hydroxide solution, the mixture was extracted with methylene chloride. The extract was washed with water, dried and evaporated. The residue was applied to column chromatography on slica gel (100 g). From Chloroform-methanol (100:1) fraction, 2-imidazolyl cyclohexanone (IIa) (2.3 g) was obtained. Mp. 104°–105° C.

IR: $\nu_{max}$ (CHCl3) 1730 cm$^{-1}$ (3) To a Grignard reagent prepared from magnesium (58 mg), 3,4-dichlorobromobenzene (537 mg) and THF (6 ml) was added dropwise a solution of Compound IIa (260 mg) in THF (10 ml). The mixture was refluxed for 1 hour, acidifid with 5% hydrochloric acid, made alkaline with 5% potassium carbonate and extracted with chloroform. The extract was washed with water and evaporated. The residue was applied to column chromatography on silica gel (6 g). From chloroform-methanol (50:1) fraction, cis-1-(3,4-chlorophenyl)-2-imidazolylcyclohexanol (21) (225 mg) was obtained (yield 46%), Mp. 198°–199° C. (acetone-ether).

Anal. calcd. for $C_{15}H_{16}N_2OCl_2$: C, 57.89; H,5.18; N,9.00; Cl,22.78 (%). Found: C,58.02; H,5.21; N,8.92; Cl,22.86 (%).

NMR: δ (CDCl3) 1.7–2.5m8H, 3.98d-d(J=12,4)1H, 6.72br2H, 7–7.36m4H ppm.

EXAMPLE 22

To a Grignard reagent prepared from anhydrous THF (30 ml), magnesium (880 mg) and p-chlorobromobenzene (6.95 g) was added dropwise a solution of 2-(1,2,4-triazol-1-yl)cyclohexanone (IIb) (5.0 g) in THF (35 ml) at room temperature with stirring. The mixture was made to react at room temperature for 2 hours and the solvent was removed by evaporation. After addition of water, the residue was extracted with chloroform. The extract was washed with water, dried and evaporated. The residue was applied to column chromatography on silica gel (80 g). From chroloform-methanol (100:1) fraction, cis-1-(4-chlorophenyl)-2-(1,2,4-triazol-1-yl)cyclohexanol (5.21 g) was obtained as crystal (yield 62%). Mp. 128°–130° C. (ether-hexane).

NMR: δ (CDCl3) 1.6–2.6br8H, 4.52d-d(J=12, 4)1H, 4.95s1H, 7.17s4H, 7.68s1H, 7.8s1H ppm.

EXAMPLE 23

(1) To a solution of cycloheptene (VII) (10 g) in methylene chloride (400 ml) was added 85% m-chloroperbenzoic acid (23 g) in small portions with stirring under ice-cooling. The mixture was made to react at 3°–10° C. for 10 hours and at room temperature for 3 hours and after removal of the precipitated benzoic acid by filtration, washed with methylene chloride. The filtrate and the washings were combined and washed with an aqueous solution of sodium thiosulfate, 5% potassium carbonate and water successively, dried and evaporated to give cycloheptene oxide (Vb).

A mixture of the product, propanol (30 ml) and imidazole (8.5 g) was refluxed for 20 hour under heating and the propanol was removed by evaporation. After addition of a small amount of water, the reaction mixture was extracted with chloroform. The extract was washed with a saturated aqueous solution of sodium chloride, dried and evaporated to give an oily residue. The residue was applied to column chromatography on silica gel (60 g). From chloroform fraction, the starting material (4.41 g) was recovered and from chloroform-methanol (50:1) fraction, trans-2-imidazolylcycloheptanol (IVc) (3.96 g) was obtained as an oil (yield 21%).

NMR: δ (CDCl3) 1.73n10H, 2.12br2H, 5.27s1H, 6.77s1H, 6.83s1H, 7.27s1H ppm.

(2) Dimethylsulfoxide (2.57 g) was mixed with methylene chloride (20 ml), cooled to −76° C. with stirring, wherein a diluted solution of anhydrous trifluoroacetic acid (6.0 g) in methylene chloride (10 ml) was added dropwise. The mixture was stirred for 1.5 hours under cooling and a solution of Compound IVc (3.96 g) in methylene chloride (25 ml) was added dropwise. The mixture was made to react at −76°–0° C. for 1 hour, cooled to −60° C. and after dropwise addition of triethylamine (9 ml), stirred for 1 hour at −60°-5° C. Water was added to the reaction mixture. The mixture was made alkaline with 5% sodium hydroxide and extracted with methylene chloride. The extract was washed with water, dried and evaporated. The residue was applied to column chromatography on silica gel (40 g). From chloroform-methanol fraction (100:1), 2-imidazolylcycloheptanone (IIc) (0.77 g) was obtained. Mp. 68°-69° C.

IR: $\nu_{max}$ (CHCl$_3$) 1720 cm$^{-1}$

NMR: δ (CDCl$_3$) 1.4–2.2m8H, 2.57m2H, 4.97d-d(J=8, 5)1H, 6.85d(J=1)1H, 7.38d(J=1)1H ppm.

(3) To a solution of Grignard reagent prepared from anhydrous THF (6 ml), magnesium (45 mg) and p-fluorobromobenzene (200 mg) was added dropwise a solution of Compound IIc (200 mg) prepared in the above (2) in THF (8 ml) under refluxing. The mixture was refluxed for 1 hour with stirring and then evaporated. After addition of water, the residue was extracted with chloroform. The extract was washed with water, dried and evaporated. The residue was applied to column chromatography on silica gel (6 gl). From chloroform-methanol (50:1) fraction, cis-1-(4-fluorophenyl)-2-imidazolylcycloheptanol (23) (180 mg) was obtained as crystal Mp. 164°-165° C.

NMR: δ (CDCl$_3$) 1.7–2.6m10H, 3.98d-d(J=11, 2)1H, 3.9br1H, 6.63brs2H, 6.7–7.2m5H ppm.

EXAMPLE 24

(1) Cycloheptene oxide (Vb) prepared from cycloheptene (10 g) in the same manner as in Example 23(1), propanol (25 ml) and 1,2,4-triazole (8.6 g) were made to react at 100° C. for 4 hours and the propanol was removed by evaporation. After addition of a small amount of water, the reaction mixture was extracted with chloroform. The residue was washed with a saturated aqueous solution of sodium chloride, dried and evaporated.

The residue was recrystallized from ether-hexane to give 2-(1,2,4-triazole-1-yl)cycloheptanol (IVd) (13.3 g) melting at 85°-86° C. (yield 35.8%).

NMR: δ (CDCl$_3$) 1.6–2m10H, 4br2H, 5.0s1H, 7.73s1H, 8.03s1H ppm.

(2) A solution of dimethylsulfoxide (1.05 g) in methylene chloride (10 ml) was cooled to −78° C. and a solution of trifluoroacetic anhydride (1.65 ml) in methylene chloride (4 ml) was added dropwise thereto with stirring. The mixture was stirred for 1 hour under cooling. A solution of Compound IVd (1.63 g) in methylene chloride (18 ml) was added dropwise thereto. The mixture was made to react at −76°-10° C. for 1.5 hours, after cooling to −65° C., mixed with triethylamine (3.75 ml) and stirred at −65°-0° C. for 1 hour. The reaction mixture was made alkaline with 5% potassium hydroxide and extracted with methylene chloride. The residue was washed with water, dried and evaporated. The residue was applied to column chromatography on silica gel (30 g). From chloroform-methanol (100:1) fraction, 1-(1,2,4-triazol-1-yl)cycloheptanone (IId) (1.16 g) was obtained (yield 72%). Mp. 82°-82.5° C. (ether-hexane).

IR: $\nu_{max}$ (CHCl$_3$) 1720 cm$^{-1}$

NMR: δ (CDCl$_3$) 1.5–2.3m8H, 2.65m2H, 5.28d-d (J=12, 5)1H, 7.91s1H, 8.22s1H ppm.

(3) To a Grignard reagent prepared from anhydrous THF (20 ml), magnesium (835 mg) and p-chlorobromobenzene (6.57 g) was added dropwise a solution of Compound IId (4.1 g) in THF (35 ml) under cooling. The mixture was made to react at room temperature for 1 hour, after addition of water, acidified with 5% hydrochloric acid, made alkaline with 5% potassium carbonate solution and then extracted with benzene. The extract was washed with water, dried and evaporated. The residue was applied to column chromatography on silica gel (70 g). From the ether fraction, cis-1-(4-chlorophenyl)-2-(1,2,4-triazol-1-yl)cycloheptanol (24) (3.6 g) was obtained as crystals (yield 54%). Mp. 129°-131° C. (acetone-hexane).

Anal. calcd. for C$_{15}$H$_{18}$N$_3$OCl: C,61.75; H,6.22; N,14.40; Cl,12.15 (%). Found: C,61.71; H,6.22; N,14.31; Cl12.45 (%).

EXAMPLES 25–35

The following compounds were obtained by the same procedure as in the above examples.

TABLE 11

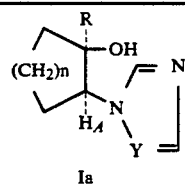

Ia

| Example No | R | n | Y | Mp (°C.) | NMR: δ (CDCl$_3$ J=Hz) H$_A$ | OH |
|---|---|---|---|---|---|---|
| 25 | Phenyl | 2 | N | 147-8 | 4.52d-d(J=12, 4) | 4.83s |
| 26 | 4-Chlorophenyl | 2 | CH | 171-3 | 3.96d-d(J=12, 4) | 4.0(Broad) |
| 27 | 4-Chlorophenyl | 3 | CH | 163-4 | 4.0d-d(J=11, 2) | 3.6(broad) |
| 28 | 4-Fluorophenyl | 2 | N | 112-3 | 4.40d-d(J=12, 4) | 4.87s |
| 29 | 4-Fluorophenyl | 2 | CH | 183-4 | 3.92d-d(J=12, 4) | 5.2s |
| 30 | 4-Fluorophenyl | 3 | N | 152-3 | 3.98d-d(J=11, −1) | 3.9(broad) |
| 31 | 3-Chlorophenyl | 2 | N | 154-7 | 4.60d-d(J=12, 4) | 4.87s |
| 32 | 2-Chlorpheny | 2 | N | 142-3 | 5.70d-d(J=12, 4) | 5.0s |
| 33 | 3,4-Dichlorophenyl | 2 | N | 158-160 | 4.52d-d(J=12, 4) | 5.0s |
| 34 | 3,4-Dichlorophenyl | 3 | N | 178-9 | 4.50d-d(J=11, −1) | 4.96s |
| 35 | 2,5-Dichlorophenyl | 2 | N | 221-2 | 5.45d-d(J=12, 4) | 5.93s |

EXAMPLE 36

Five parts of Compound 22, 20 parts of propylene alcohol, 5 parts of polyethylene alkyl phenyl ether and 70 parts of water are mixed and dissolved to give a solution, which is diluted with water so that the effective concentration of Compound 22 is 50-500 ppm, and sprayed foliarly.

EXAMPLE 37

Fifty parts of Compound 24, 6 parts of sodium alkyl benzenesulfonate, 4 parts of sodium lignine sulfonate and 40 parts of clay are mixed and crushed to give a wettable powder, which is diluted so that the effective concentration of Compound 24 is 50-500 ppm, and sprayed on fruit.

EXAMPLE 38

Five parts of Compound 28, 90 parts of an equal-weight mixture of bentonite and talc and 5 parts of sodium alkyl benzenesulfonate are mixed, crushed and formulated to granules.

EXAMPLE 39

Twenty-five parts of Compound 30, 8 parts of polyoxyethylene alkyl phenyl ether, 2 parts of sodium alkyl benzenesulfonate and 65 parts of xylene are mixed and disslved to give a concentrated emulsion, which is diluted so that the effective concentration of Compound 30 is 50-5000 ppm and sprayed foliarly.

EXAMPLE 40

One part of Compound 1 is mixed with 99 parts of talc to give a dust.

EXAMPLE 41

A solution is prepared in the same manner as in Example 36 using Compound 33 instead of Compound 22.

EXAMPLE 42

A wettable powder is prepared in the same manner as in Example 37 using Compound 34 instead of Compound 24.

EXAMPLE 43

Granules are prepared in the same manner as in Example 38 using Compound 35 instead of Compound 28.

What we claim is:

1. A process for preparing a compound of the formula I:

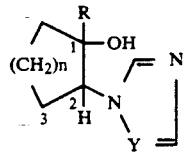

wherein R is alkyl, phenyl, benzyl, thienyl or naphthyl, which groups are unsubstituted or are substituted by one or more halogens, Y is methine or nitrilo and n is 2 or 3 with the proviso that azolyl and hydroxy are in cis configuration when R is phenyl or halogenophenyl, or an acid addition salt thereof which comprises reacting a cycloalkane of the formula II

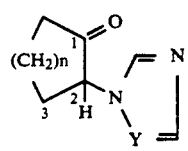

wherein Y and n are each as defined above with a compound of the formula III;

RZ     III wherein Z is a halomagnesium or an alkali metal and R is the same as defined above to obtain the cis-isomer of the compound of formula I as the main product.

* * * * *